United States Patent
Platte et al.

(10) Patent No.: US 12,133,970 B2
(45) Date of Patent: Nov. 5, 2024

(54) DRUG INJECTION DEVICE AND RECYCLING SYSTEM

(71) Applicants: Covestro LLC, Pittsburgh, PA (US); Covestro Deutschland AG, Leverkusen (DE)

(72) Inventors: Isaac Platte, Pittsburgh, PA (US); Mark Matsco, Monaca, PA (US); Pierre Moulinie, Oakdale, PA (US); Lauren Zetts, Pittsburgh, PA (US); Paul Nowatzki, Pittsburgh, PA (US); Marc Uerdingen, Lohmar (DE)

(73) Assignees: Covestro LLC, Pittsburgh, PA (US); Covestro Deutschland AG, Leverkusen (DE)

( * ) Notice: Subject to any disclaimer, the term of this patent is extended or adjusted under 35 U.S.C. 154(b) by 0 days.

(21) Appl. No.: 18/570,293

(22) PCT Filed: Jul. 25, 2022

(86) PCT No.: PCT/US2022/038144
§ 371 (c)(1),
(2) Date: Dec. 14, 2023

(87) PCT Pub. No.: WO2023/009417
PCT Pub. Date: Feb. 2, 2023

(65) Prior Publication Data
US 2024/0277939 A1 Aug. 22, 2024

Related U.S. Application Data

(60) Provisional application No. 63/226,459, filed on Jul. 28, 2021.

(30) Foreign Application Priority Data

Aug. 10, 2021 (EP) .................................... 21190465

(51) Int. Cl.
*A61M 5/20* (2006.01)
*A61L 31/06* (2006.01)
(Continued)

(52) U.S. Cl.
CPC ............ *A61M 5/2033* (2013.01); *A61L 31/06* (2013.01); *A61M 2005/2026* (2013.01);
(Continued)

(58) Field of Classification Search
CPC . A61M 5/2033; A61M 2005/206; A61M 5/24
See application file for complete search history.

(56) References Cited

U.S. PATENT DOCUMENTS 4,394,863 A * 7/1983 Bartner ............... A61M 5/2066
604/157
5,514,097 A * 5/1996 Knauer ............. A61M 5/31538
604/218
(Continued)

FOREIGN PATENT DOCUMENTS

JP 3399524 B2 * 4/2003 ................ A61J 1/00
WO WO-2015007822 A1 * 1/2015 ........ A61M 5/31528

*Primary Examiner* — William R Carpenter
(74) *Attorney, Agent, or Firm* — John E. Mrozinski, Jr.

(57) ABSTRACT

A drug injection device consists of a body, a cap, a striker, a spin wheel, a button, a spring, an ampoule, and optionally a needle. Each of the body, the cap, the striker, the spin wheel and the button is a molded plastic part, made out of mostly polycarbonate, which slide, snap, screw or rest in place, without the use of adhesives or fasteners. Also disclosed is a system for recycling a drug injection device having molded plastic parts made from mostly polycarbonates, comprising disassembling the drug injection device, separating the molded plastic parts from all other parts, and reprocessing the molded plastic parts together into recycled resin, which may be through regrinding, melting, and pelletizing.

15 Claims, 6 Drawing Sheets

(51) Int. Cl.
   *B29B 17/02*     (2006.01)
   *B29B 17/04*     (2006.01)
   *B29K 69/00*     (2006.01)
   *B29K 105/26*    (2006.01)

(52) U.S. Cl.
   CPC .......... *A61M 2207/00* (2013.01); *B29B 17/02* (2013.01); *B29B 17/0412* (2013.01); *B29K 2069/00* (2013.01); *B29K 2105/26* (2013.01)

(56) References Cited

U.S. PATENT DOCUMENTS

| | | |
|---|---|---|
| 8,348,905 B2 | 1/2013 | Radmer et al. |
| 10,363,373 B2 | 7/2019 | Maxfield |
| 2007/0088290 A1* | 4/2007 | Heiniger ............. A61M 5/2033 604/218 |

* cited by examiner

DRUG INJECTION DEVICE AND RECYCLING SYSTEM

CROSS REFERENCE TO RELATED APPLICATIONS

This application is a national stage application under 35 U.S.C. § 371 of PCT/US2022/038144, filed Jul. 25, 2022, which claims benefit of EP application Ser. No. 21/190,465.1, filed Aug. 10, 2021, and U.S. Provisional Application No. 63/226,459, filed Jul. 28, 2021, all of which are incorporated herein by reference in their entireties.

FIELD OF THE INVENTION

The present invention relates in general to a device for delivering a drug into a human body, and to a system for recycling a drug delivery device having a limited number of parts, and manufactured out of a minimum difference in materials.

SUMMARY OF THE INVENTION

A drug injection device consists of a body, a cap, a striker, a spin wheel, a button, a spring, an ampoule, and optionally a needle. In an embodiment, each of the parts slide, snap, screw or rest in place, preferably, the cap is attached to the body through use of a snap fitting. In another embodiment, each of the body, the cap, the striker, the spin wheel and the button is a molded plastic part. In a different embodiment, there are no adhesives or fasteners used to attach any of the body, cap, striker, spin wheel, button or spring, or even there are no adhesives or fasteners used in the drug delivery device.

In another embodiment, the spin wheel comprises one or more fins, which may be curved at one end, and straight at the other end. In yet another embodiment, the cap comprises fins, which are configured to slide along the fins of the spin wheel as the spin wheel rotates.

In an embodiment not yet disclosed, the spin wheel comprises one or more stops which prevent the striker from pushing the ampoule in a first position, and allow the striker to push the ampoule in a second position, the second position available after rotation of the spin wheel. In a different embodiment, the striker comprises one or more protrusions which extend through one or more openings in the cap.

In still another embodiment, each of the body, cap, striker, spin wheel and button comprise 50-95 wt. % polycarbonate, preferably 60-95 wt. % polycarbonate, more preferably 70-90 wt. %, or most preferably 80-90 wt. % polycarbonate. In yet another embodiment, each of the body, cap, striker, spin wheel and button further comprise greater than 0 wt. % to 5 wt. %, preferably 0.5 to 2 wt. %, of a high molecular weight non-polar lubricant and most preferably a siloxane lubricant, wherein the siloxane is not polymerized with the polycarbonate.

In another, the body, cap, striker, spin wheel and button are made of three compositions, preferably two compositions, or most preferably the same composition.

A system for recycling a drug injection device having molded plastic parts and other parts, comprises disassembling the drug injection device, separating the molded plastic parts from all other parts, and reprocessing the molded plastic parts into recycled resin, wherein each of the molded plastic parts comprise 50-95 wt, % polycarbonate.

In an embodiment, the system further comprises separating the molded plastic parts according to their composition. In another embodiment, the drug injection device consists of a body: a cap: a striker: a spin wheel: a button; a spring: an ampoule; and optionally a needle. In another, there are no adhesives or fasteners used to attach any of the body, cap, striker, spin wheel, button or spring, or in the drug delivery device.

In yet another embodiment, each of the body, cap, striker, spin wheel and button comprise 60-95 wt. % polycarbonate, preferably 70-90 wt. %, or more preferably 80-90 wt. % polycarbonate. In another, each of the body, cap, striker, spin wheel and button further comprise greater than 0 wt. % to 5 wt. %, preferably 0.5 to 2 wt. %, of a high molecular weight non-polar lubricant and most preferably a siloxane lubricant, wherein the siloxane is not polymerized with the polycarbonate. In still another embodiment, the reprocessing step comprises regrinding at least one molded plastic part, melting the at least one reground molded plastic part, and pelletizing the at least one reground and melted plastic part into recycled polycarbonate resin. In another, all of the molded plastic parts of the drug injection device are reground, melted and pelletized. In still another, all of the molded plastic parts of the drug injection device are reground together.

These and other advantages and benefits of the present invention will be apparent from the Detailed Description of the Invention herein below.

BRIEF DESCRIPTION OF THE FIGURES

The present invention will now be described for purposes of illustration and not limitation in conjunction with the figures, wherein.

DETAILED DESCRIPTION OF THE INVENTION

Drug injectors are known in the prior art. However, they generally comprise many different parts, that are each made up of different materials, and are put together in a manner that makes recycling difficult, if not impossible. Meanwhile, there exists a need, and a desire, to be able to reuse materials in useful manners, and to reduce the amount of both raw materials that are derived from natural resources, and to waste from devices that are made for a limited use. This change requires a new design for a drug injection device, which uses a minimum number of parts, where the most parts possible are made in such a manner that they can be easily assembled and disassembled, and are made of a common material that can be recycled together in a cost effective manner, to be able to be reused multiple times to reduce waste, energy, and raw materials.

The present invention provides a drug injection device, which may be used to deliver a fixed amount of a drug or other fluid into a human or other body. The device includes a body, a striker, a spin wheel, a cap, a button, a spring and an ampoule. The body, striker, spin wheel, cap and button are all made of the same or similar materials to facilitate their recycling. The present invention further includes a system for recycling the drug injection device, wherein each of the parts slide, snap or rest in place for easy assembly and disassembly, and the molded parts are easily and quickly segregated from the non-molded parts. The molded parts are then recycled and reprocessed together through grinding, melting and pelletizing.

Parts

Figure 1:
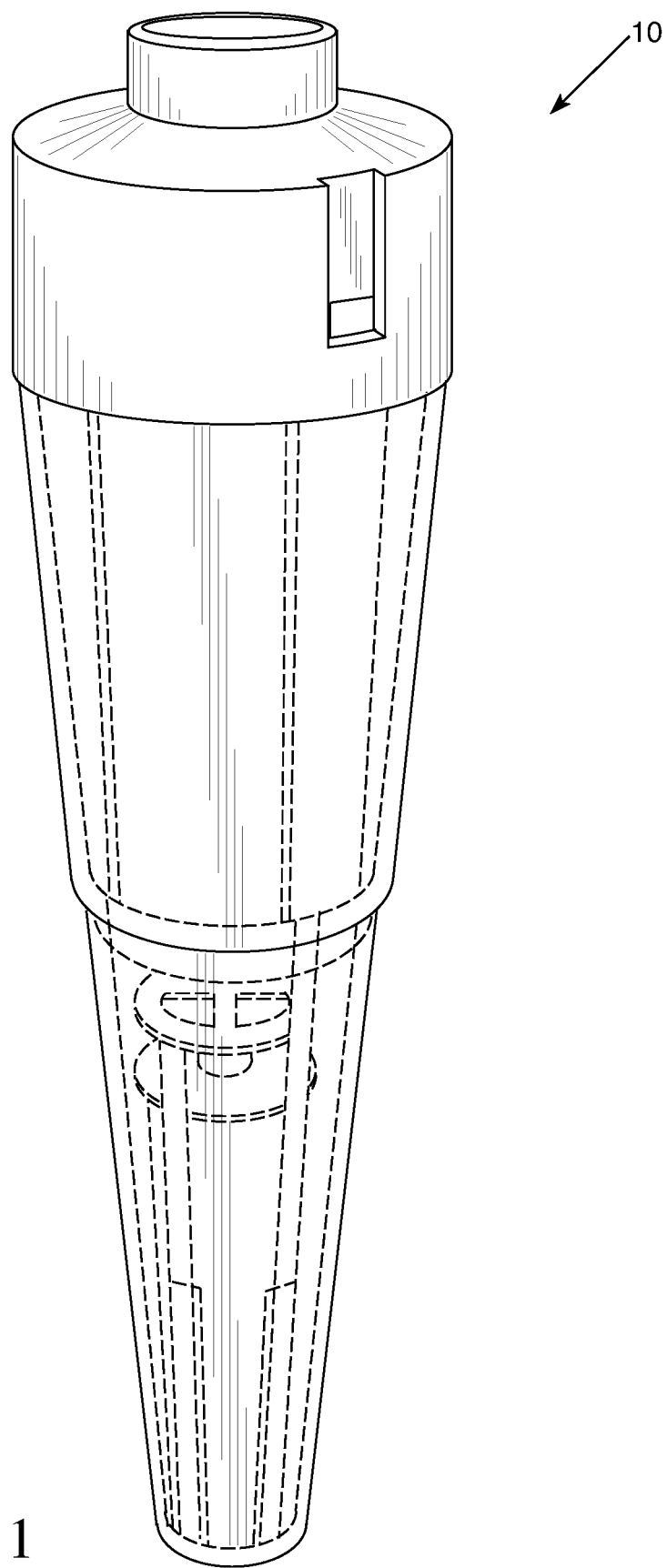
FIG. 1 is a perspective view of a drug injection device of the present invention.

An embodiment of the present invention, drug injection device 10, is shown in FIG. 1. It comprises a body, a striker, a spin wheel, a cap, a button, a spring, and an ampoule.

Figure 2:
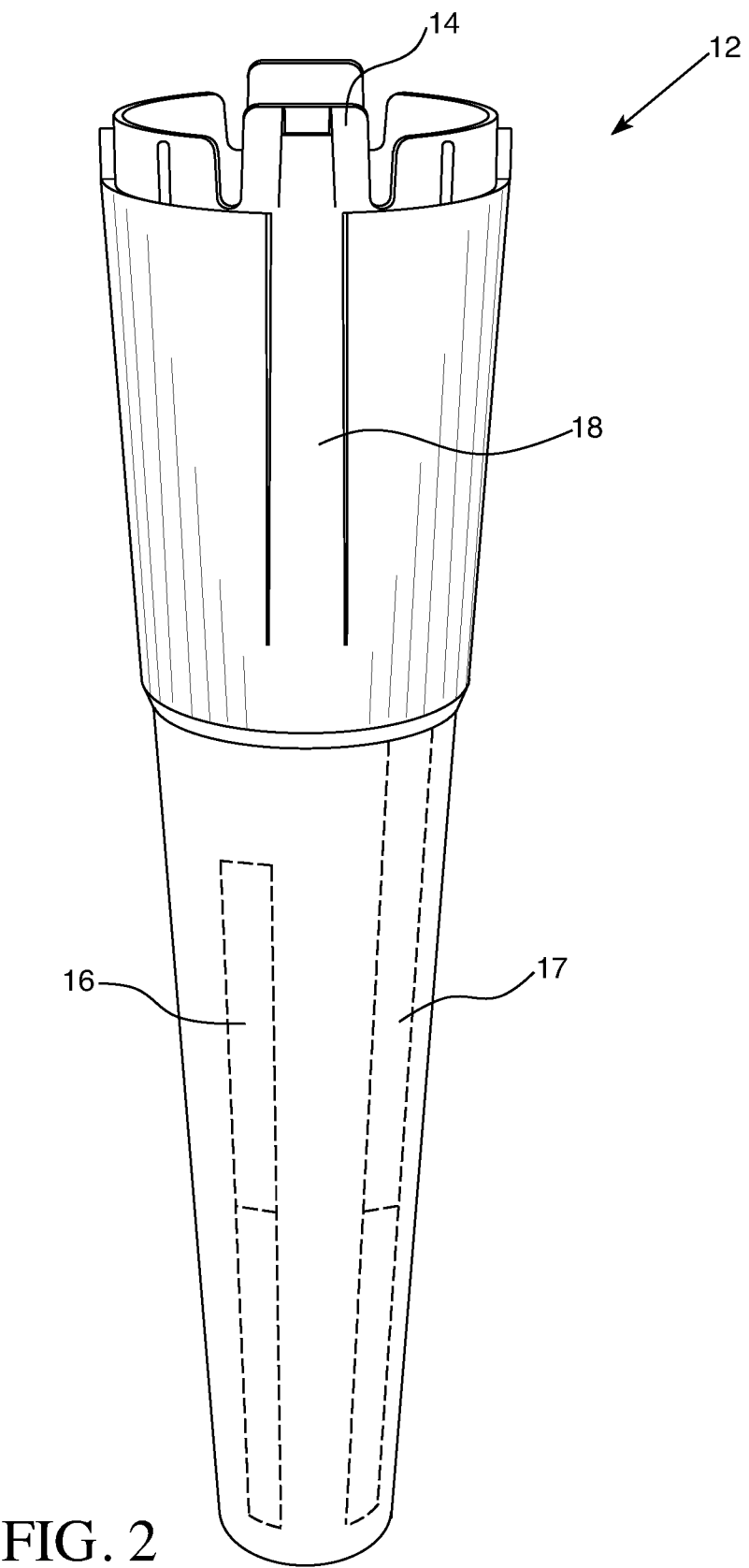
FIG. 2 is perspective view of the body of the drug injection device of FIG. 1.

As shown in FIG. 2, Body 12 is a plastic molded part that surrounds all of the other molded parts except for the cap. It can be held or gripped on the outside, without touching any of the other parts. It includes features such as snap fitting 14, recessed feature 18, fin 16 and fin 17. Snap fitting 14 includes molded features that allow the body to snap fit to the cap without any adhesive, attachment or further molding. Body 12 may further comprise molded features such as recessed feature 18 that is thicker and stronger than other areas of body 12, to make the snap fittings more durable and less likely to break away. Internal fins 16 and 17 may be made of different lengths, and may extend further inside radially in some regions rather than others. They are used as guides and stops for other parts to contact, as discussed below.

Figure 3:
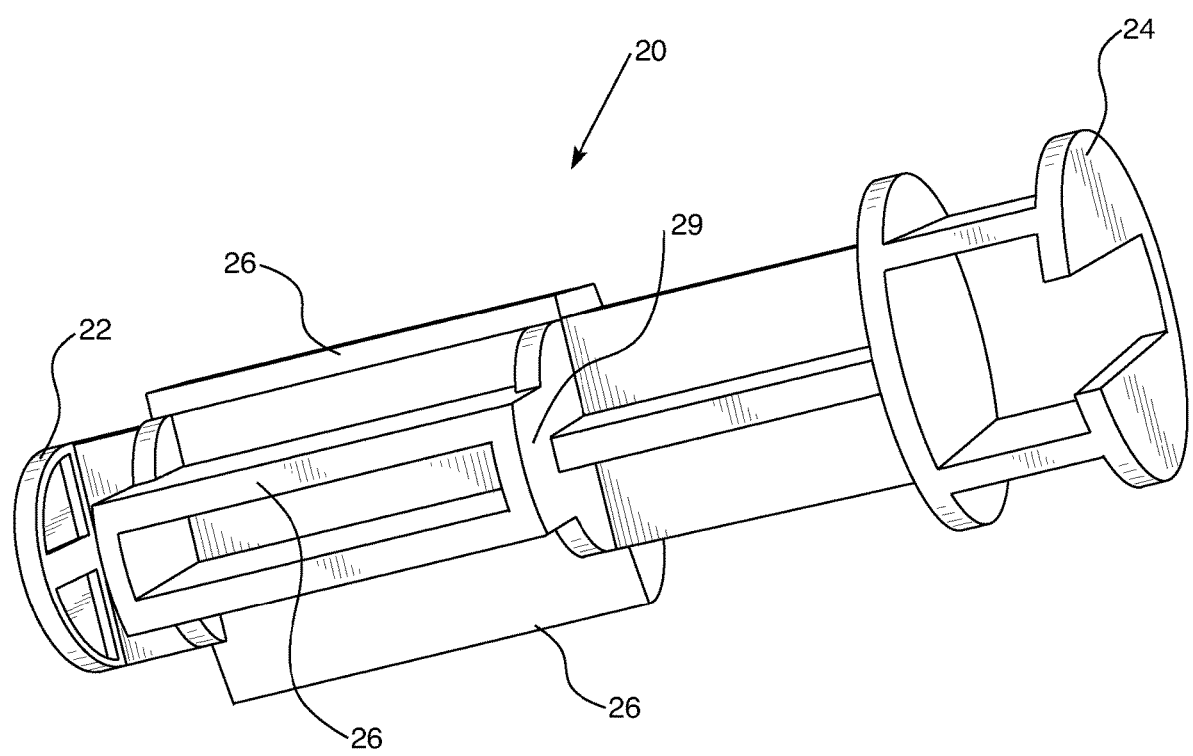
FIG. 3 is a perspective view of the striker of the drug injection device of FIG. 1.

As shown in FIG. 3, striker 20 is a molded plastic part. It comprises spring surface 22, which comes in contact with the spring, and ampoule end 24, which comes in contact with the ampoule. Striker 20 further comprises protrusions 26, and resting surface 29, which keep striker 20 in place as described below. Ampoule end 24 may comprise a slide fit, such that a molded piece of the ampoule may be easily attached and detached from striker 20.

Figure 4:
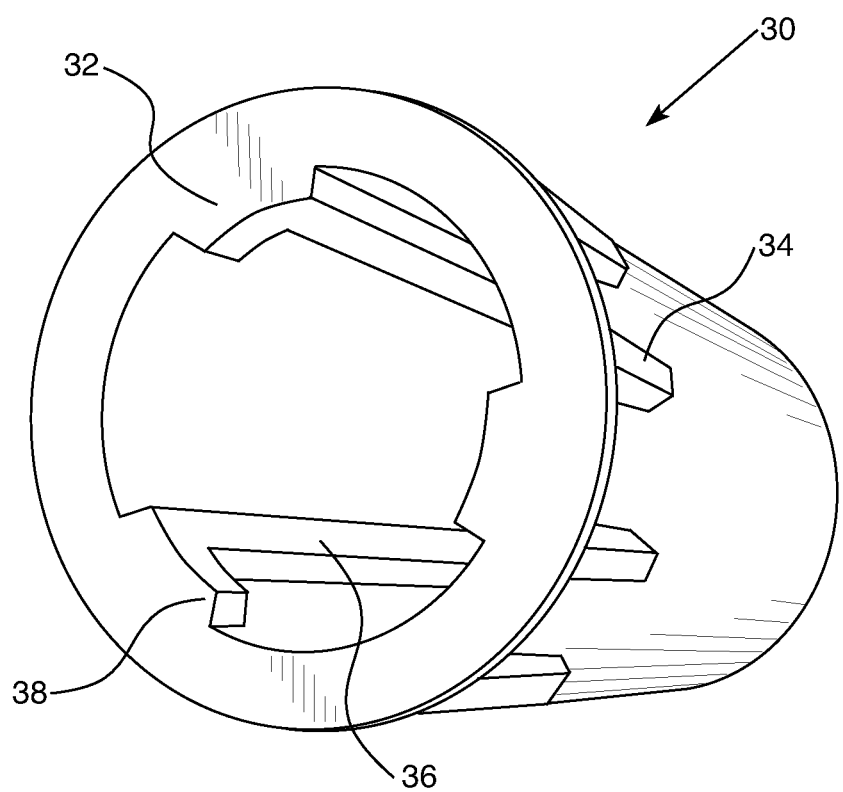
FIG. 4 is a bottom perspective view of the spin wheel of the drug injection device of FIG. 1.
Figure 5:
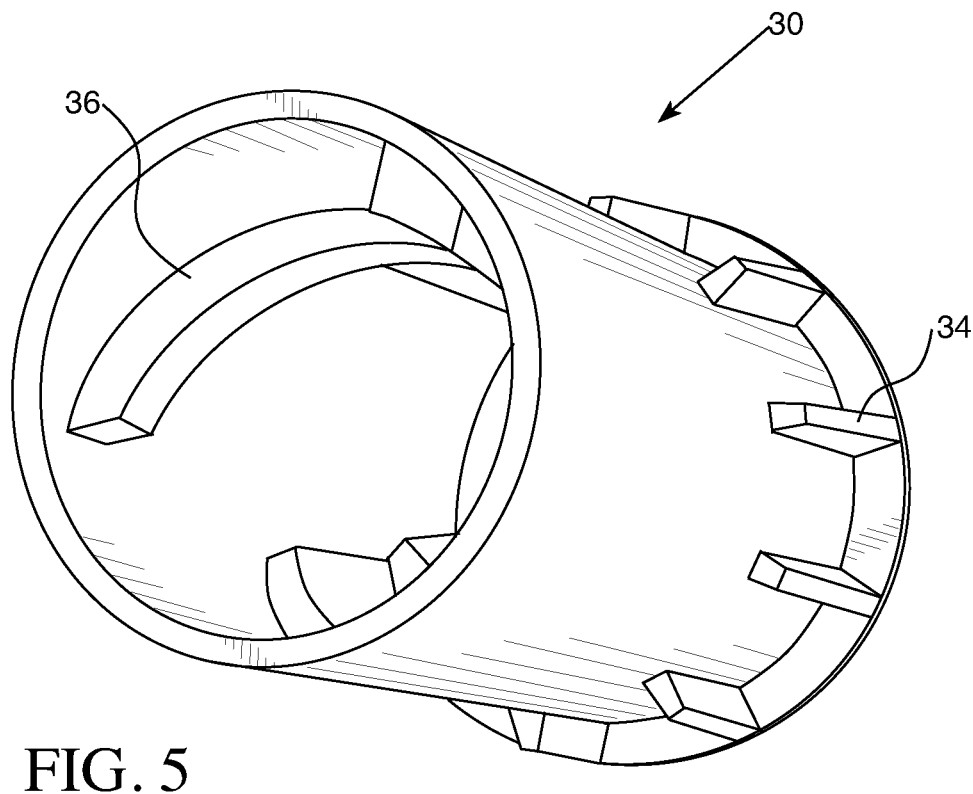
FIG. 5 is a top perspective view of the spin wheel of the drug injection device of FIG. 1.

As shown in FIGS. 4 and 5, spin wheel 30 comprises bottom surface 32, supports 34, fins 36 and stops 38. Bottom surface 32 is wider, and flares out, to ensure it will be in a particular position within body 12. Bottom surface 32 is sized such that it rests at a particular position in body 12, which is tapered and comprises internal elements to hold spin wheel 30 at a particular level within the device, to be able to work with the other components. Supports 34 keep the bottom surface from moving over time. Fins 36 are curved at the top, and then are straight towards the bottom, to work with features on the button to delay the spring's movement, as described below in association with the button. While the button does not turn radially, the spin wheel does spin radially in place as the spin wheel reacts to the position of the button. Stops 38 halt the button after actuation, and are sized and placed according to the distance required for the ampoule and needle to travel to deliver the drug into the patient.

Figure 6:
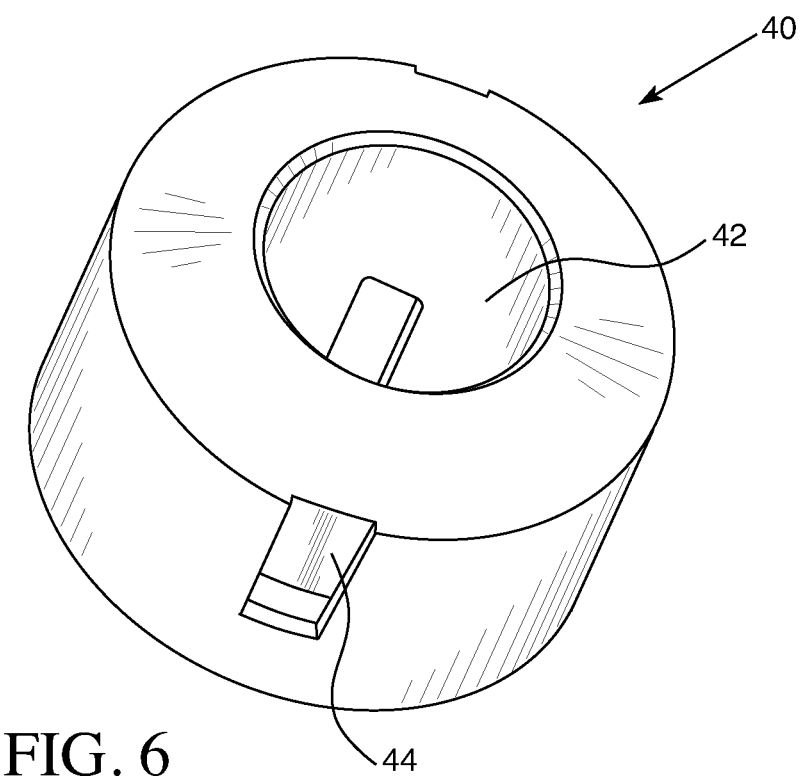
FIG. 6 is a top perspective view of the cap of the drug injection device of FIG. 1.
Figure 7:
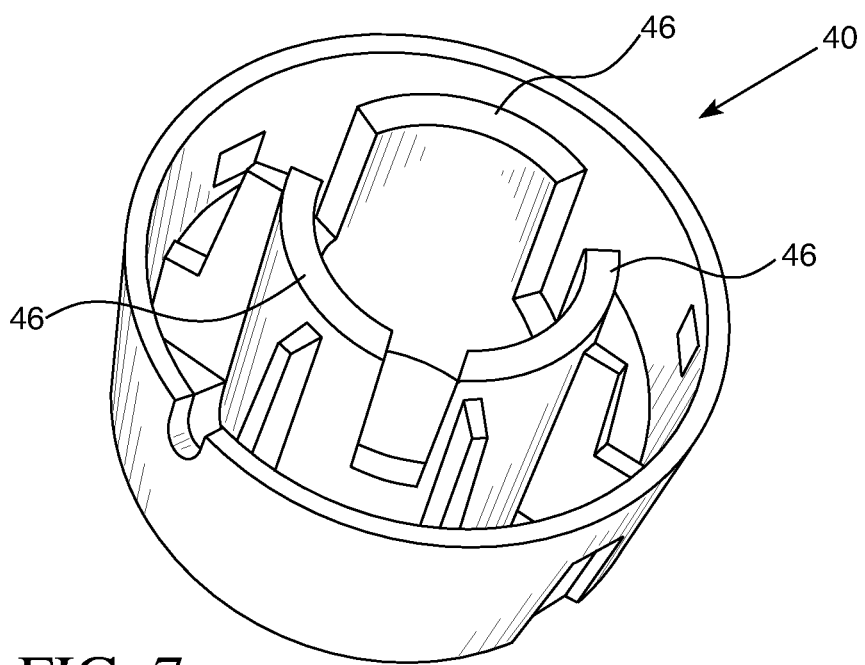
FIG. 7 is a bottom perspective view of the cap of the drug injection device of FIG. 1.

As shown in FIGS. 6 and 7, cap 40 comprises center cavity 42, through which the top of the button is located in the drug delivery device. Snap fittings 44 may be indents with holes, to work with the snap fittings on the body. The interior of cap 40 includes inside supports 46, which are not only made to define center cavity 42, but also to provide a surface for the top of the spin wheel, so it may remain in place, even if the drug delivery device were turned upside down.

Figure 8:
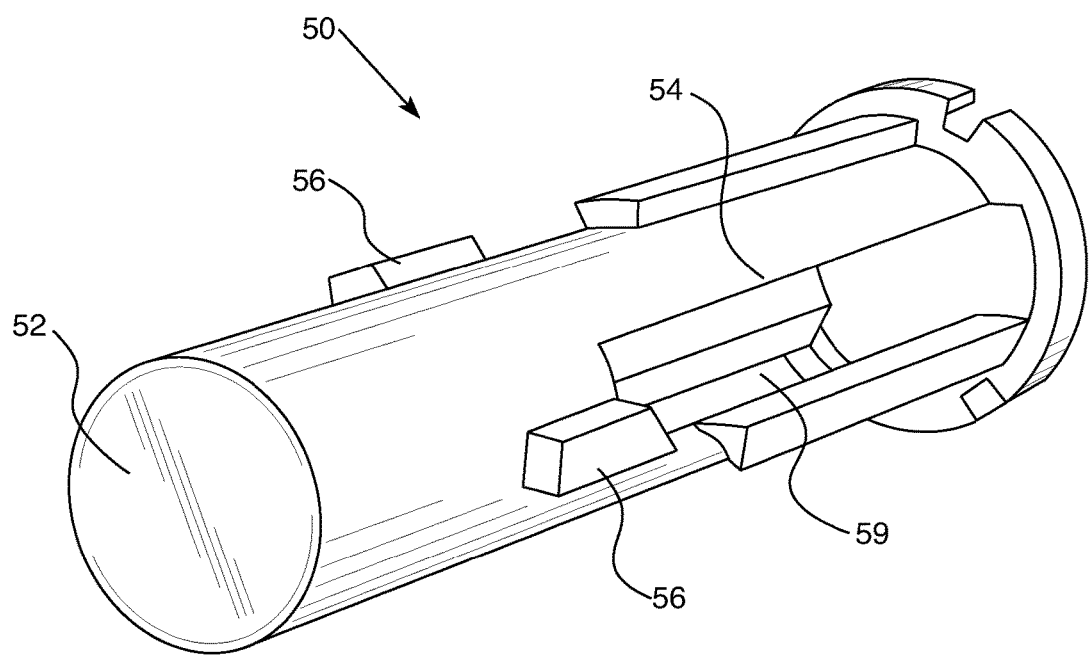
FIG. 8 is a top perspective view of the button of the drug injection device of FIG. 1.
Figure 9:
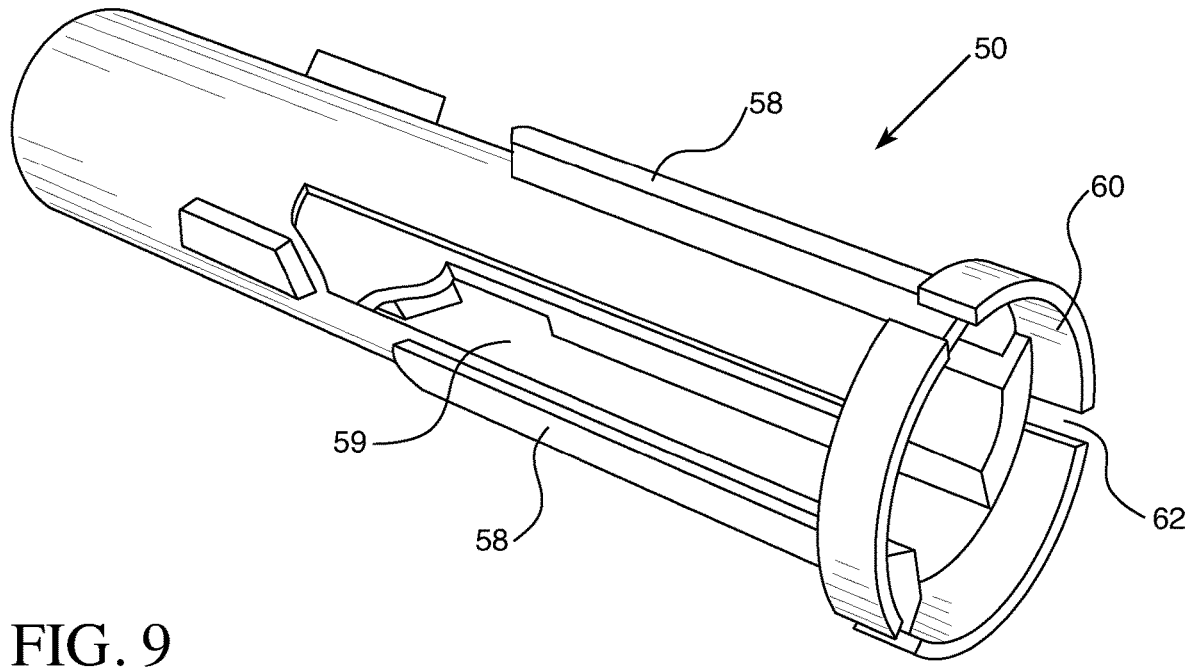
FIG. 9 is a bottom perspective view of the button of the drug injection device of FIG. 1.

As shown in FIGS. 8 and 9, button 50 comprises pressing surface 52, shaft 54, upper fins 56, lower fins 58, lower surface 60 and openings 62. Pressing surface 52 is where a user would actuate the device to inject the patient. A spring (not shown) is inserted, and is disposed between the inside surface of pressing surface 52 and spring surface 22 of striker 20. Before actuation, the curved portion of fin 36 of spin wheel 30, as shown in FIG. 5, is located between upper fin 56 and lower fin 58.

Not shown in the figures is the spring, which in a preferred embodiment is a simple metal spring. Also not shown is the ampoule, which is attached to the striker. The ampoule contains the drug to be administered. Attached to it, or part of it, is the needle which goes into the patient to deliver the drug. Neither the ampoule, the needle, or the metal spring, are considered to be molded parts for purposes of this application. While the ampoule may contain molded parts, it likely cannot be recycled in the same manner due to the drugs that it contains. Furthermore, it is also unlikely to be constructed of the same materials, because of its function to contain the drug to be administered.

In a preferred embodiment, there are no adhesives or fasteners used to attach any of the molded parts, or the spring, either within the parts themselves, or to attach to other molded parts. In another embodiment, there are no adhesives or fasteners used in the drug delivery device.

To activated the device, a user depresses pressing surface 52, upper fins 56 press against the fins 36 of spin wheel 30. This action adds resistance to the user pressing the button, and offers a tactile sensation to the user, as the spring compresses, but the striker has not yet moved. Before actuation, striker 20 is kept in place horizontally, by resting surface 29 being on top of stop 38. Protrusions 26 keep striker 20 in place vertically, by their placement inside openings 59 of button 50. As spin wheel 30 rotates during actuation, upper fins 56 slide downward upon fin 36, until fin 36 no longer offers any horizontal resistance because of its shape. At a certain point after rotation of spin wheel 30, fin 36 is completely vertical between upper fins 56 and lower fins 58, offering no resistance at all to the button as it is depressed. Meanwhile, stop 38 of spin wheel 30 rotates away from resting surface 29 of striker 20, while striker 20 remains in place vertically because of the placement of protrusions 26 disposed within openings 59 of cap 50. When stop 38 of spin wheel 30 is rotated completely away from resting surface 29 of striker 20, then there is nothing to hold striker 20 back from the force of the spring, disposed between cap 50 and striker 20, pushing striker 20 against the ampoule to deliver the drug to the patient. While spin wheel 30 rotates during actuation, none of button 50, striker 20 or the ampoule rotate.

After actuation, the device may be reset into position ready for actuation, by pressing the ampoule, and thus striker 20 and the spring, towards and against button 50 and cap 40. As protrusions 26 ascend towards cap 40, and through openings 59, protrusions 26 press against fins 36 of spin wheel 30, rotating spin wheel 30. During this time, protrusions 26 are located in between upper fins 56 and lower fins 58 of button 50. As protrusions 26 ascend to the top of openings 59 in cap 50, fins 36 of spin wheel 30 will rotate below protrusions 26 to the position before actuation. At this point, fins 36 of spin wheel 30, are located between upper fin 56 and lower fin 58 of cap 50, and keep protrusions 26 of striker 20 from moving vertically. The user can hear a click from fins 36 getting back into place, and feel the lack of force against the ampoule, as the striker is held back into place by the positioning of fins 36.

Materials

The molded parts discussed above, the body, striker, spin wheel, cap and button, are made of a molded plastic material, and preferably substantially the same plastic material. Preferably, each of these components comprise 50-100% the same material. In other preferred embodiments, the components comprise at least 60%, at least 70%, or at least 80% the same material. In a preferred embodiment, the molded parts comprise at least 90% of the same material, or even 100% the same material.

While a variety of plastics may be used in association with the present invention, polycarbonate is a preferred material, given its strength, versatility, and ease of recycling.

Aromatic polycarbonates and/or aromatic polyester carbonates that are suitable are known in the literature or can be prepared by processes known in the literature (for the preparation of aromatic polycarbonates see, for example, Schnell, "Chemistry and Physics of Polycarbonates", Interscience Publishers, 1964 and DE-AS 1 495 626, DE-A 2 232 877, DE-A 2 703 376, DE-A 2 714 544, DE-A 3 000 610, DE-A 3 832 396; for the preparation of aromatic polyester carbonates see e.g. DE-A 3 007 934).

The preparation of aromatic polycarbonates is carried out, for example, by reaction of diphenols with carbonic acid halides, preferably phosgene, and/or with aromatic dicarboxylic acid dihalides, preferably benzenedicarboxylic acid dihalides, according to the interfacial process, optionally using chain terminators, for example monophenols, and optionally using branching agents having a functionality of three or more than three, for example triphenols or tetraphenols. Preparation by a melt polymerization process by reaction of diphenols with, for example, diphenyl carbonate is also possible.

Diphenols for the preparation of the aromatic polycarbonates and/or aromatic polyester carbonates are preferably those of formula (I)

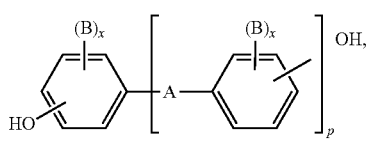

wherein
A is a single bond, C1- to C5-alkylene, C2- to C5-alkylidene, C5- to C6-cyclo-alkylidene, O, SO—, —CO—, —S—, —SO2—, C6- to C12-arylene, to which further aromatic rings optionally containing heteroatoms can be fused, or a radical of formula (II) or (III)

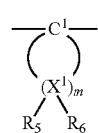

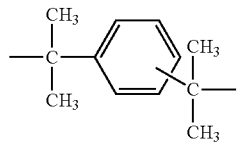

B is in each case C1 to C12-alkyl, preferably methyl, halogen, preferably chlorine and/or bromine,
x each independently of the other is 0, 1 or 2,
p is 1 or 0, and
R5 and R6 can be chosen individually for each X1 and each independently of the other is hydrogen or C1 to C6-alkyl, preferably hydrogen, methyl or ethyl,
X1 is carbon and
m is an integer from 4 to 7, preferably 4 or 5, with the proviso that on at least one atom X1, R5 and R6 are simultaneously alkyl.

Preferred diphenols are hydroquinone, resorcinol, dihydroxydiphenols, bis-(hydroxyphenyl)-$C_1$-$C_5$-alkanes, bis-(hydroxyphenyl)-$C_5$-$C_6$-cycloalkanes, bis-(hydroxyphenyl) ethers, bis-(hydroxyphenyl) sulfoxides, bis-(hydroxyphenyl) ketones, bis-(hydroxyphenyl)-sulfones and α, α-bis-(hydroxyphenyl)-diisopropyl-benzenes, and derivatives thereof brominated and/or chlorinated on the ring.

Particularly preferred diphenols are 4,4'-dihydroxy diphenyl, bisphenol A, 2,4-bis(4-hydroxy-phenyl)-2-methylbutane, 1, 1-bis-(4-hydroxyphenyl)-cyclohexane, 1, 1-bis-(4-hydroxy-phenyl)-3,3,5-trimethylcyclohexane, 4,4'-dihydroxydiphenyl sulfide, 4,4'-dihydroxydiphenylsulfone and di- and tetra-brominated or chlorinated derivatives thereof, such as, for example, 2,2-bis(3-chloro-4-hydroxyphenyl)-propane, 2,2-bis-(3,5-dichloro-4-hydroxyphenyl)-propane or 2,2-bis-(3,5-dibromo-4-hydroxyphenyl)-propane. 2,2-Bis-(4-hydroxyphenyl)-propane (bisphenol A) is particularly preferred.

The diphenols can be used on their own or in the form of arbitrary mixtures. The diphenols are known in the literature or are obtainable according to processes known in the literature.

Chain terminators suitable for the preparation of thermoplastic aromatic polycarbonates are, for example, phenol, p-chlorophenol, p-tert-butylphenol or 2,4,6-tribromophenol, but also long-chained alkylphenols, such as 4-[2-(2,4,4-trimethylpentyl)]-phenol, 4-(1,3-tetramethyl-butyl)-phenol according to DE-A 2 842 005 or monoalkylphenol or dialkylphenols having a total of from 8 to 20 carbon atoms in the alkyl substituents, such as 3,5-di-tert-butyl-phenol, p-isooctylphenol, p-tert-octylphenol, p-dodecylphenol and 2-(3,5-dimethylheptyl)-phenol and 4-(3,5-dimethylheptyl)-phenol. The amount of chain terminators to be used is generally from 0.5 mol % to 10 mol %, based on the molar sum of the diphenols used in a particular case.

The thermoplastic aromatic polycarbonates have mean molecular weights (weight-average Mw, measured by GPC (gel permeation chromatography) with polycarbonate standard) of from 15,000 to 80,000 g/mol, preferably from 19,000 to 32,000 g/mol, particularly preferably from 22,000 to 30,000 g/mol.

The thermoplastic aromatic polycarbonates can be branched in a known manner, preferably by the incorporation of from 0.05 to 2.0 mol %, based on the sum of the diphenols used, of compounds having a functionality of three or more than three, for example those having three or more phenolic groups. Preference is given to the use of linear polycarbonates, more preferably based on bisphenol A.

Both homopolycarbonates and copolycarbonates are suitable. For the preparation of copolycarbonates of component A it is also possible to use from 1 to 25 wt. %, preferably from 2.5 to 25 wt. %, based on the total amount of diphenols to be used, of polydiorganosiloxanes having hydroxyaryloxy end groups. These are known (U.S. Pat. No. 3,419,634) and can be prepared according to processes known in the literature. Also suitable are copolycarbonates containing polydiorganosiloxanes; the preparation of copolycarbonates containing polydiorganosiloxanes is described, for example, in DE-A 3 334 782.

Aromatic dicarboxylic acid dihalides for the preparation of aromatic polyester carbonates are preferably the diacid dichlorides of isophthalic acid, terephthalic acid, diphenyl ether 4,4'-dicarboxylic acid and naphthalene-2,6-dicarboxylic acid.

Mixtures of the diacid dichlorides of isophthalic acid and terephthalic acid in a ratio of from 1:20 to 20:1 are particularly preferred.

In the preparation of polyester carbonates, a carbonic acid halide, preferably phosgene, is additionally used concomitantly as bifunctional acid derivative.

Suitable chain terminators for the preparation of the aromatic polyester carbonates, in addition to the monophenols already mentioned, are also the chlorocarbonic acid esters thereof and the acid chlorides of aromatic monocarboxylic acids, which can optionally be substituted by $C_1$ to $C_{22}$-alkyl groups or by halogen atoms, as well as aliphatic $C_2$ to $C_{22}$-monocarboxylic acid chlorides.

The amount of chain terminators is in each case from 0.1 to 10 mol %, based in the case of phenolic chain terminators on mol of diphenol and in the case of monocarboxylic acid chloride chain terminators on mol of dicarboxylic acid dichloride.

One or more aromatic hydroxycarboxylic acids can additionally be used in the preparation of aromatic polyester carbonates.

The aromatic polyester carbonates can be both linear and branched in known manner (see in this connection DE-A 2 940 024 and DE-A 3 007 934), linear polyester carbonates being preferred.

There can be used as branching agents, for example, carboxylic acid chlorides having a functionality of three or more, such as trimesic acid trichloride, cyanuric acid trichloride, 3,3',4,4'-benzophe-none-tetracarboxylic acid tetrachloride, 1,4,5,8-naphthalene-tetracarboxylic acid tetrachloride or pyromellitic acid tetrachloride, in amounts of from 0.01 to 1.0 mol % (based on dicarboxylic acid dichlorides used), or phenols having a functionality of three or more, such as phloroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri-(4-hydroxyphenyl)-ethane, tri-(4-hydroxyphenyl)-phenylmethane, 2,2-bis[4,4-bis(4-hydroxy-phenyl)-cyclohexyl]-propane, 2,4-bis(4-hydroxyphenyl-isopropyl)-phenol, tetra-(4-hydroxy-phenyl)-methane, 2,6-bis(2-hydroxy-5-methyl-benzyl)-4-methyl-phenol, 2-(4-hydroxyphenyl)-2-(2,4-dihydroxyphenyl)-propane, tetra-(4-[4-hydroxyphenyl-isopropyl]-phenoxy)-methane, 1,4-bis[4,4'-dihydroxy-triphenyl)-methyl]-benzene, in amounts of from 0.01 to 1.0 mol %, based on diphenols used. Phenolic branching agents can be placed in a vessel with the diphenols; acid chloride branching agents can be introduced together with the acid dichlorides.

The content of carbonate structural units in the thermoplastic aromatic polyester carbonates can vary as desired. The content of carbonate groups is preferably up to 100 mol %, in particular up to 80 mol %, particularly preferably up to 50 mol %, based on the sum of ester groups and carbonate groups. Both the esters and the carbonates contained in the aromatic polyester carbonates can be present in the polycondensation product in the form of blocks or distributed randomly.

The thermoplastic aromatic polycarbonates and polyester carbonates can be used on their own or in an arbitrary mixture. In various embodiments of the invention, the molded materials comprise 50-95%, 60-95%, 70-90% or 80-90% polycarbonate.

In an embodiment, the molded materials further comprise a siloxane-based lubricant, a siloxane polymer that improves internal lubrication and that also helps to bolster the wear and friction properties of the composition encountering another surface. Any of a variety of siloxane polymers may generally be employed. The siloxane polymer may, for instance, encompass any polymer, co-polymer or oligomer that includes siloxane units in the backbone having the formula:

$$RrSiO_{(4-r/2)}$$

wherein
R is independently hydrogen or substituted or unsubstituted hydrocarbon radicals, and
r is 0, 1, 2 or 3.

Some examples of suitable radicals R include, for instance, alkyl, aryl, alkylaryl, alkenyl or alkynyl, or cycloalkyl groups, optionally substituted, and which may be interrupted by heteroatoms, i.e., may contain heteroatom(s) in the carbon chains or rings. Suitable alkyl radicals, may include, for instance, methyl, ethyl, n-propyl, isopropyl, n-butyl, isobutyl, tert-butyl, n-pentyl, isopentyl, neopentyl and tert-pentyl radicals, hexyl radicals (e.g., n-hexyl), heptyl radicals (e.g., n-heptyl), octyl radicals (e.g., n-octyl), isooctyl radicals (e.g., 2,2,4-trimethylpentyl radical), nonyl radicals (e.g., n-nonyl), decyl radicals (e.g., n-decyl), dodecyl radicals (e.g., n-dodecyl), octadecyl radicals (e.g., n-octadecyl), and so forth. Likewise, suitable cycloalkyl radicals may include cyclopentyl, cyclohexyl cycloheptyl radicals, methylcyclohexyl radicals, and so forth: suitable aryl radicals may include phenyl, biphenyl, naphthyl, anthryl, and phenanthryl radicals: suitable alkylaryl radicals may include o-, m- or p-tolyl radicals, xylyl radicals, ethylphenyl radicals, and so forth; and suitable alkenyl or alkynyl radicals may include vinyl, 1-propenyl, 1-butenyl, 1-pentenyl, 5-hexenyl, butadienyl, hexadienyl, cyclopentenyl, cyclopentadienyl, cyclohexenyl, ethynyl, propargyl 1-propynyl, and so forth. Examples of substituted hydrocarbon radicals are halogenated alkyl radicals (e.g., 3-chloropropyl, 3,3,3-trifluoropropyl, and perfluorohexylethyl) and halogenated aryl radicals (e.g., p-chlorophenyl and p-chlorobenzyl). In one particular embodiment, the siloxane polymer includes alkyl radicals (e.g., methyl radicals) bonded to at least 70 mol % of the Si atoms and optionally vinyl and/or phenyl radicals bonded to from 0.001 to 30 mol % of the Si atoms. The siloxane polymer is also preferably composed predominantly of diorganosiloxane units. The end groups of the polyorganosiloxanes may be trialkylsiloxy groups, in particular the trimethylsiloxy radical or the dimethylvinylsiloxy radical. However, it is also possible for one or more of these alkyl groups to have been replaced by hydroxy groups or alkoxy groups, such as methoxy or ethoxy radicals. Particularly suitable examples of the siloxane polymer include, for instance, dimethylpolysiloxane, phenylmethylpolysiloxane, vinylmethylpolysiloxane, and trifluoropropylpolysiloxane.

The siloxane polymer may also include a reactive functionality on at least a portion of the siloxane monomer units of the polymer, such as one or more of vinyl groups, hydroxyl groups, hydrides, isocyanate groups, epoxy groups, acid groups, halogen atoms, alkoxy groups (e.g., methoxy, ethoxy and propoxy), acyloxy groups (e.g., acetoxy and octanoyloxy), ketoximate groups (e.g., dimethylketoxime, methylketoxime and methylethylketoxime), amino groups (e.g., dimethylamino, diethylamino and butylamino), amido groups (e.g., N-methylacetamide and N-ethylacetamide), acid amido groups, amino-oxy groups, mercapto groups, alkenyloxy groups (e.g., vinyloxy, isopropenyloxy, and 1-ethyl-2-methylvinyloxy), alkoxyalkoxy groups (e.g., methoxyethoxy, ethoxyethoxy and methoxypropoxy), aminoxy groups (e.g., dimethylaminoxy and diethylaminoxy), mercapto groups, etc.

Regardless of its particular structure, the siloxane polymer typically has a relatively high molecular weight, which reduces the likelihood that it migrates or diffuses to the surface of the polymer composition and thus further minimizes the likelihood of phase separation. For instance, the siloxane polymer typically has a weight average molecular weight of about 100,000 grams per mole or more, in some embodiments about 200,000 grams per mole or more, and in some embodiments, from about 500,000 grams per mole to about 2,000,000 grams per mole. The siloxane polymer may also have a relative high kinematic viscosity, such as about 10,000 centistokes or more, in some embodiments about 30,000 centistokes or more, and in some embodiments, from about 50,000 to about 500,000 centistokes.

If desired, silica particles (e.g., fumed silica) may also be employed in combination with the siloxane polymer to help improve its ability to be dispersed within the composition. Such silica particles may, for instance, have a particle size of from about 5 nanometers to about 50 nanometers, a surface area of from about 50 square meters per gram (m2/g) to about 600 m2/g, and/or a density of from about 160 kilogram per cubic meter (kg/m3) to about 190 kg/m3. When employed, the silica particles typically constitute from about 1 to about 100 parts, and in some some embodiments, from about 20 to about 60 parts by weight based on 100 parts by weight of the siloxane polymer. In one embodiment, the silica particles can be combined with the siloxane polymer prior to addition of this mixture to the polymer composition. For instance a mixture including an ultrahigh molecular weight polydimethylsiloxane and fumed silica can be incorporated in the polymer composition.

In a preferred embodiment, the siloxane is not polymerized with the polycarbonate. In another preferred embodiment, the siloxane is not a coating of any other component, but rather a separate component within the composition, which can be mixed about within the composition, independent of any other component in the composition.

The siloxane may be present in the thermoplastic molding composition in an amount of greater than 0 to 5 wt. %, preferably 0.5 to 2 wt. % of the thermoplastic molding composition of the plastic molded parts.

The plastic molded parts may comprise conventional polymer additives, such as flame-retardant additives and synergists, antidripping agents, lubricants and release agents (for example pentaerythritol tetrastearate), nucleating agents, stabilizers (for example UV/light stabilizers, heat stabilizers, antioxidants, transesterification inhibitors, hydrolytic stabilizers), antistatics (for example conductive blacks, carbon fibers, carbon nanotubes as well as organic antistatics such as polyalkylene ethers, alkyl sulfonates or polyamide-containing polymers) as well as colorants, pigments, fillers, talc and reinforcing materials, in particular glass fibers, mineral reinforcing materials and carbon fibers.

As well as comprising optional further additives, particularly preferred molding compositions comprise a release agent, particularly preferably pentaerythritol tetrastearate, in an amount of from 0.1 to 1.5 parts by weight, preferably from 0.2 to 1.0 part by weight, particularly preferably from 0.3 to 0.8 part by weight. As well as comprising optional further additives, particularly preferred molding compositions comprise at least one stabilizer, for example selected from the group of the sterically hindered phenols, phosphites and mixtures thereof and particularly preferably Irganox® B900, in an amount of from 0.01 to 0.5 part by weight, preferably from 0.03 to 0.4 part by weight, particularly preferably from 0.06 to 0.3 part by weight.

As noted above, the composition of the plastic molded part may further comprise an anti-dripping agent polytetrafluoroethylene (PTFE) or PTFE-containing compositions such as, for example, masterbatches of PTFE with styrene- or methyl-methacrylate-containing polymers or copolymers, in the form of powders or in the form of a coagulated mixture.

The fluorinated polyolefins used as antidripping agents have a high molecular weight and have glass transition temperatures of over −30° C., generally over 100° C., fluorine contents of preferably from 65 to 76 wt. %, in particular from 70 to 76 wt. %, mean particle diameters $d_{50}$ of from 0.05 to 1000 µm, preferably from 0.08 to 20 µm. In general, the fluorinated polyolefins have a density of from 1.2 to 2.3 g/cm³. Preferred fluorinated polyolefins are polytetrafluoroethylene, polyvinylidene fluoride, tetrafluoroethylene/hexafluoropropylene and ethylene/tetrafluoroethylene copolymers. The fluorinated polyolefins are known (see "Vinyl and Related Polymers" by Schildknecht, John Wiley & Sons, Inc., New York, 1962, pages 484-494: "Fluorpolymers" by Wall, Wiley-Interscience, John Wiley & Sons, Inc., New York, Volume 13, 1970, pages 623-654; "Modern Plastics Encyclopedia", 1970-1971, Volume 47, No. 10 A, October 1970, McGraw-Hill, Inc., New York, pages 134 and 774; "Modern Plastics Encyclopedia", 1975-1976 October 1975, Volume 52, No. 10 A, McGraw-Hill, Inc., New York, pages 27, 28 and 472 and US-PS 3 671 487, 3 723 373 and 3 838 092).

They can be prepared by known processes, for example by polymerization of tetrafluoroethylene in an aqueous medium with a free-radical-forming catalyst, for example sodium, potassium or ammonium peroxodisulfate, at pressures of from 7 to 71 kg/cm² and at temperatures of from 0 to 200° C., preferably at temperatures of from 20 to 100° C. (For further details see e.g. U.S. Pat. No. 2,393,967.) Depending on the form in which they are used, the density of these materials can be from 1.2 to 2.3 g/cm³, and the mean particle size can be from 0.05 to 1000 µm.

The fluorinated polyolefins that are preferred have mean particle diameters of from 0.05 to 20 µm, preferably from 0.08 to 10 µm, and density of from 1.2 to 1.9 g/cm³.

Suitable fluorinated polyolefins which can be used in powder form are tetrafluoroethylene polymers having mean particle diameters of from 100 to 1000 µm and densities of from 2.0 g/cm³ to 2.3 g/cm³. Suitable tetrafluoroethylene polymer powders are commercial products and are supplied, for example, by DuPont under the trade name Teflon®.

As well as comprising optional further additives, particularly preferred flame-retardant compositions comprise a fluorinated polyolefin in an amount of from 0.05 to 5.0 parts by weight, preferably from 0.1 to 2.0 parts by weight, particularly preferably from 0.3 to 1.0 part by weight of the composition of the plastic molded part.

There are certain materials that are not molded plastic parts, or such parts may be molded, but cannot comprise the same materials, or the materials cannot be recycled in the same manner. Notably, the spring is preferably a metal. The ampoule containing the drug to be injected may be glass or a molded plastic. The needle associated with the ampoule that enters the body is likely made of a metal material.

Recycling

As noted above, the body and the cap are snap fit together, while the remaining parts slide in place, and are kept in position by fitting in between fins or other features of the parts themselves. This design improves recyclability, as it makes for easy disassembly. A user simply unsnaps the cap from the body, removes the cap, then the spin wheel, button, spring, striker and ampoule from the body. A needle may also be attached to the ampoule. The ampoule and needle will likely have to be disposed of in another manner due to the drug residue inside of it, or contact with human blood. The molded parts: the body, cap, spin wheel, striker and button, can be combined for recycling together. In an embodiment, the molded parts are made of two or three different types of material. As an alternative to recycling each of the molded components together, the molded components may be separated according to their materials of construction.

The recycled molded parts may be ground together, melted and pelletized into a recycled plastic resin, and molded into recycled parts to create another plastic part or another device of the present invention. Other systems and methods of recycling may also be employed, including chemical cracking, to revert the polycarbonate into its building blocks of bisphenol A and other components. Alternatively, solvents may be used to disassemble plastic parts, and each component or constituent within each plastic may be extracted or recovered.

Aspects of the present invention include:
1. A drug injection device consisting of: a body: a cap: a striker; a spin wheel: a button: a spring: an ampoule; and optionally a needle.
2. The drug injection device of 1, wherein each of the parts slide, snap, screw or rest in place.
3. The drug injection device of 2, wherein the cap is attached to the body through use of a snap fitting.
4. The drug injection device of any of the above aspects, wherein each of the body, the cap, the striker, the spin wheel and the button is a molded plastic part.
5 The drug injection device of any of the above aspects, wherein there are no adhesives or fasteners used to attach any of the body, cap, striker, spin wheel, button or spring.
6. The drug injection device of any of the above aspects, wherein there are no adhesives or fasteners used in the drug delivery device.
7 The drug injection device of any of the above aspects, wherein the spin wheel comprises one or more fins.
8. The drug injection device of any of the above aspects, wherein the fins are curved at one end, and straight at the other end.
9 The drug injection device of any of the above aspects, wherein the cap comprises fins, which are configured to slide along the fins of the spin wheel as the spin wheel rotates.
10. The drug injection device of any of the above aspects, wherein the spin wheel comprises one or more stops which prevent the striker from pushing the ampoule in a first position, and allow the striker to push the ampoule in a second position, the second position available after rotation of the spin wheel.
11. The drug injection device of any of the above aspects, wherein the striker comprises one or more protrusions which extend through one or more openings in the cap.
12. The drug injection device of any of the above aspects, wherein each of the body, cap, striker, spin wheel and button comprise 50-95 wt. % polycarbonate, preferably 60-95 wt. % polycarbonate, more preferably 70-90 wt. %, or most preferably 80-90 wt. % polycarbonate.
13. The drug injection device of 12, wherein each of the body, cap, striker, spin wheel and button further comprise greater than 0 wt. % to 5 wt. %, preferably 0.5 to 2 wt. %, of a high molecular weight non-polar lubricant and most preferably a siloxane lubricant, wherein the siloxane is not polymerized with the polycarbonate.
14. The drug injection device of any of the above aspects, wherein the body, cap, striker, spin wheel and button are made of three compositions, preferably two compositions, or most preferably the same composition.
15. A system for recycling a drug injection device having molded plastic parts and other parts, comprising:
disassembling the drug injection device;
separating the molded plastic parts from all other parts; and
reprocessing the molded plastic parts into recycled resin, wherein each of the molded plastic parts comprise 50-95 wt, % polycarbonate.
16. The system of 15, further comprising separating the molded plastic parts according to their composition.
17. The system of 15 or 16, where the drug injection device consists of a body; a cap: a striker; a spin wheel: a button: a spring: an ampoule; and optionally a needle.
18. The system of 17, wherein there are no adhesives or fasteners used to attach any of the body, cap, striker, spin wheel, button or spring.
19. The system of any of 15-18, wherein there are no adhesives or fasteners used in the drug delivery device.
20. The system of any of 15-19, wherein each of the body, cap, striker, spin wheel and button comprise 60-95 wt. % polycarbonate, preferably 70-90 wt. %, or more preferably 80-90 wt. % polycarbonate.
21. The system of 20, wherein each of the body, cap, striker, spin wheel and button further comprise greater than 0 wt. % to 5 wt. %, preferably 0.5 to 2 wt. %, of a high molecular weight non-polar lubricant and most preferably a siloxane lubricant, wherein the siloxane is not polymerized with the polycarbonate.
22. The system of any of 15-21, wherein the reprocessing step comprises:
regrinding at least one molded plastic part;
melting the at least one reground molded plastic part, and
pelletizing the at least one reground and melted plastic part into recycled polycarbonate resin.
23. The system of 22, wherein all of the molded plastic parts of the drug injection device are reground, melted and pelletized.
24. The system of 22 or 23, wherein all of the molded plastic parts of the drug injection device are reground together.

What is claimed is:
1. A drug injection device (10) comprising:
a tapered body (12) having a center cavity surrounding a striker (20), a rotating spin wheel (30),
a button (50),
a spring, and
an ampoule,
optionally, a needle attached to the ampoule,
wherein the tapered body (12) is provided with a snap fitting (14) at one end thereof receiving a cap (40) comprising a center cavity, and wherein the tapered body (12) optionally is provided with one or more recessed features (18) and one or more internal fins (16, 77) within the center cavity,
wherein the striker (20) comprises a spring surface and an ampule end and wherein the striker (20) contacts the spring at the spring surface (22) and contacts the ampoule at the ampoule end (24),
wherein the rotating spin wheel (30) comprises a top, a bottom surface (32), and one or more supports (34), and wherein the bottom surface (32) is wider than the top, and wherein the rotating spin wheel (30) is capable of rotation during actuation of the drug injection device (10),
wherein the button (50) comprises a pressing surface (52), a shaft (54), one or more upper fins (56), one or more lower fins (58), a lower surface (60), and one or more openings (62) and wherein the button (50) is located within the center cavity (42) of the cap (40), wherein the spring is disposed between the pressing surface (52) of the button (50) and the spring surface (22) of the striker (20),
wherein the ampoule contains a drug to be administered and contacts the striker (20), and
wherein each of the tapered body (12), the cap (40), the striker (20), the rotating spin wheel (30) and the button (50) comprise a molded plastic part.

2. The drug injection device (10) according to claim 1, wherein each of the tapered body (12), the cap (40), the striker (20), the rotating spin wheel (30), and the button (50) slide, snap, screw, or rest in place.

3. The drug injection device (10) according to claim 1, wherein the cap (40) is attached to the tapered body (12) with a snap fitting (44).

4. The drug injection device (10) according to claim 3, wherein the cap (40) comprises one or more fins, which are configured to slide along the one or more fins (36) of the rotating spin wheel (30) as the rotating spin wheel (30) rotates.

5. The drug injection device (10) according to claim 1, wherein no adhesives or fasteners attach any of the tapered body (12), cap (40), striker (20), rotating spin wheel (30), button (50), or spring.

6. The drug injection device (10) according to claim 1, wherein the rotating spin wheel (30) comprises one or more fins (36).

7. The drug injection device (10) according to claim 6, wherein the one or more fins (36) are curved at a first end, and straight at a second end.

8. The drug injection device (10) according to claim 1, wherein the rotating spin wheel (30) comprises one or more stops (38) which prevent the striker (20) from pushing the ampoule in a first position, and allow the striker (20) to push the ampoule in a second position, wherein the second position is available after rotation of the rotating spin wheel (30).

9. The drug injection device (10) according to claim 1, wherein the striker (20) comprises one or more protrusions (26) which extend through one or more openings in the cap (40).

10. The drug injection device (10) according to claim 1, wherein each of the tapered body (12), the cap (40), the striker (20), the rotating spin wheel (30), and the button (50) comprise 50-95 wt. % polycarbonate.

11. The drug injection device (10) according to claim 10, wherein each of the body (12), the cap (40), the striker (20), the rotating spin wheel (30), and the button (50) further comprise greater than 0 wt. % to 5 wt. % of a high molecular weight non-polar lubricant.

12. A process of recycling the drug injection device (10) according to claim 1 having molded plastic parts and other parts, the process comprising:
    disassembling the drug injection device (10);
    separating the molded plastic parts from all other parts; and
    reprocessing the molded plastic parts into recycled resin, wherein each of the molded plastic parts comprise 50-95 wt, % polycarbonate.

13. The process according to claim 12, further comprising separating the molded plastic parts according to their composition.

14. The process according to claim 12, wherein the reprocessing comprises:
    regrinding at least one molded plastic part to form at least one reground molded plastic part;
    melting the at least one reground molded plastic part to form at least one reground and melted plastic part; and
    pelletizing the at least one reground and melted plastic part into recycled polycarbonate resin.

15. The process according to claim 12, wherein all the molded plastic parts of the drug injection device are reground, melted, and pelletized.

* * * * *